United States Patent [19]

Peiffer

[11] Patent Number: 5,093,448
[45] Date of Patent: Mar. 3, 1992

[54] POLYMERIZABLE CATIONIC VISCO-ELASTIC MONOMER FLUIDS

[75] Inventor: Dennis G. Peiffer, East Brunswick, N.J.

[73] Assignee: Exxon Research and Engineering Company, Florham Park, N.J.

[21] Appl. No.: 537,839

[22] Filed: Jun. 13, 1990

Related U.S. Application Data

[62] Division of Ser. No. 135,596, Dec. 21, 1987, abandoned.

[51] Int. Cl.$^5$ ............................................ C08F 265/04
[52] U.S. Cl. .................................................... 526/310
[58] Field of Search ......................................... 526/310

[56] References Cited

U.S. PATENT DOCUMENTS

| | | | |
|---|---|---|---|
| 4,460,758 | 7/1984 | Peiffer et al. | 526/287 |
| 4,528,348 | 7/1985 | Turner et al. | 526/225 |

*Primary Examiner*—Joseph L. Schofer
*Assistant Examiner*—Jeffrey T. Smith
*Attorney, Agent, or Firm*—Richard E. Nanfeldt; Joseph J. Dvorak

[57] ABSTRACT

The synthesis of a novel family of cationic monomers capable of forming viscoelastic fluids are described within. These monomers are formed primarily through the reaction of allyl halides and dimethyl alkylamines. The rheological properties of the fluids can be dramatically modified with changes in alkyl length and/or counterion structure. In addition, it is noted that these viscoelastic fluids have properties quite similar to conventional polymer solutions even though the former structures are held together through physical forces and not through chemical bonding as in the latter materials. In addition, the properties of this unique family of cationic monomers are capable of forming viscoelastic fluids in high brine solutions. Even though the counterion attached to the monomer contributes greatly to the rheological properties, addition of soluble acid, bases and salts do not destroy (through ion exchange mechanisms) the viscoelastic properties of these fluids.

4 Claims, 8 Drawing Sheets

POLYMERIZABLE CATIONIC VISCO-ELASTIC MONOMER FLUIDS

This is a division of application Ser. No. 135,596, filed 12/21/87, now abandoned, 04/22/91.

BACKGROUND OF THE INVENTION

It is well known that polymeric materials are generally considered useful as viscosification agents when dissolved in an appropriate solvent system. The major reason for this viscosity enhancement is due to the very large dimensions of the individual polymer chain as compared to the dimension of the single solvent molecules. Any increase in the size of the polymer chain will produce a corresponding enhancement in the viscosity of the solution. This effect is maximized when the polymer is dissolved in a "good" solvent. Therefore, in general, a soluble polymer is useful for thickening solvents, while a water soluble polymer is appropriate for increasing the viscosity of aqueous systems. With regard to aqueous solutions, solvent soluble nonionic polymers and high charge density sulfonated or carboxylate polyelectrolytes are quite useful in this regard and are commonly used materials. However, the solution properties of the former family of materials are controlled primarily through modification of the molecular weight of the polymer and through changes in the level of dissolved polymer. These materials become especially effective at concentrations where the individual polymer chains begin to overlap. This "transition" is commonly referred to in the literature polymer chains begin to overlap concentration or simply C*. It should be noted that in most nonionic polymers of commercial interest, a relatively large amount of polymer is required prior to reaching C*. Therefore, this approach is undesirable from an economic viewpoint. Moreover, the rheological properties of many of these nonionic systems have been published. The results of these studies shown that, in general, these solutions are shear thinning over all shear rates investigated.

Polyelectrolytes, on the other hand, are very useful and the most commonly used materials. However, the solution properties of these materials begin to deteriorate as low molecular additives (i.e., acids, bases or salts) are dissolved in the solution. These additives screen the charges that are fixed along the chain backbone which results in a decrease in the dimensions of the polymer molecule. The viscosity diminishes as long as the chain continue to shrink.

It has been found previously (U.S. Pat. Nos. 4,460,758 and 4,540,496), for example, that intrapolymer complexes, composed of a nonstoichometic ratio cationic and anionic monomeric units, can be useful in viscosifying aqueous solutions systems (as required in a variety of well control and workover fluids; i.e., water based drilling fluids and acid gelation systems). More importantly, these polymeric materials possess higher viscosity in acid, base or salt solution than in the corresponding fresh water system. Even more interesting is the observation that these polymeric materials show a corresponding viscosity enhancement as the concentration of the dissolved acid, base or salt is increased, even though the polyampholyte contains a substantial amount of dissociable charge. As explained earlier, these viscosity results are unexpected since the general tendency of charged macromolecules in these types of aqueous solutions shows a marked decrease in thickening efficiency.

Furthermore, in recent years, interpolymer complexes have received considerable attention in the literature due to their interesting and unique properties. In most instances, these complexes are formed by intimately mixing aqueous solutions containing high-charge density polyelectrolytes possessing opposite charge. When these polymer molecules meet in solution, the interaction between oppositely charged sites will cause the release of their associated counterions forming the complex. The counterions are now free to diffuse into the bulk solution. Normally, phase separation occurs upon prolonged standing in these high-charged density complexes. As a result, these materials have poor viscosification properties. In previous U.S. patents it is reported that low-charge interpolymer complexes are soluble and effective in viscosifying aqueous solution systems. More importantly, these complexes possess a substantially higher viscosity than the corresponding individual low-charge density copolymer components. As detailed earlier, these characteristics are unexpected since high-charge density complexes are insoluble in these conventional solution systems.

Even more interesting is the unique and unexpected result that these soluble interpolymer complexes are capable of enhancing the viscosity of aqueous solutions under relatively broad shear conditions. With these unique polymeric materials, dilatant behavior occurs in aqueous fluids which are of extreme technological utility. It is further noted that under the identical experimental conditions, the viscosity of the individual copolymer components show the normal shear thinning behavior.

Shear thickening fluids are rare and have mostly been demonstrated in suspensions. [1] Polymer solutions and melts are known, on the other hand, to exhibit strong shear thinning behavior, while most liquids of lower molecular weight are Newtonian.

[1] W. H. Bauer and E. A. Collins in "Rheology," Vol. 4, edited R. R. Eirich, page 459, Academic Press, 1967.

A polymer which was introduced by ICI (FM-9) as an antimisting agent for jet fuel was shown to be "progressively shear thickening." work done by S. T. J. Peng and R. F. Landel [2] at Jet Propulsion Laboratories under an FAA contract for antimisting in jet fuels showed that subjecting a solution of FM-9 in jet fuel at about 0.3–1.0 weight % polymer to steady shearing will produce viscous growth with time. It was found that the time scale and the extent of thickening can be accelerated by either increasing the concentration or by increasing the shear rate. The composition of FM-9 is not disclosed by ICI or by other agents working with this polymer.

[2] S. T. J. Peng and R. F. Landel, J. Appl. Phys., 52, 5988 (1981).

Peng and Landel correlate antimisting behavior with shear thickening or with high elongational viscosity which is exhibited by fluids that are able to demonstrate flow in a tubeless siphon. [3]

[3] S. T. J. Peng and R. F. Landel in "Rheology," Vol. 2, edited by G. Astarita, page 385, Plenum Press, 1980.

However, as previously noted, polymeric materials are useful as viscosity enhancers when dissolved in the appropriate solvent system. The principal reason for this behavior is due primarily to the large volume which a single macromolecular chain can occupy within the solvent. An increase in the size of the chain produces a concomitant enhancement in the solution viscosity.

However, when the polymer chain is placed in a shear field, segmental orientation takes place in the direction of the shearing force. The viscosity of the fluid dramatically drops due to this orientation phenomena. This is a typical behavior of most solutions containing dissolved polymeric materials. However, if the polymer molecule has a high molecular weight with a relatively flexible backbone and the solvent viscosity is sufficiently high, different behavior is anticipated.

It has been shown by several groups [4] that with increasing shear rates the viscosity should show a decrease, followed by a minimum value and a subsequent increase in cases where both solvent viscosity and polymer molecular weight are very high. This latter effect gives rise to dilatant behavior. However, the above mentioned conditions required for the appearance of shear thickening behavior in these polymeric solution systems are not applicable for many technologically interesting fluids. In most of the common synthetic polymers, it is difficult from a synthetic viewpoint to obtain sufficiently high molecular weight and, in addition, most solvents (for example, water) have rather low viscosities.

[4] O. Quadrat, Adv. Colloid Interface Sci., 24, 45 (1985).

The instant invention teaches that a novel family of cationic-alkyl containing monomers, i.e. polymerizable moieties, form large structures in solution. The dimensions of these structures are comparable to those of polymeric chains. As a result, these structures, formed from these monomers are useful and very effective viscosifiers for aqueous solutions. In addition, these monomers have markedly unique and improved solution properties, as compared to conventional water soluble polymers. These fluids formed with these monomers can adequately be described as polymerizable cationic viscoelastic monomer fluids.

In addition, these monomers have markedly unique and improved solution properties in high brine environments, as compared to conventional water soluble polymers.

These monomers are based on, but not limited to, the incorporation of the above cationic monomers into an aqueous fluid system.

In addition, these monomers are not incorporated into a polymer chain structure via conventional synthetic techniques to form hydrophobically and associating type polymers. Very effective rheological control is assured even without the need to form a hydrophobically-associating polymer.

It should be noted in this regard that the use of hydrophobic groups on water soluble polymers to enhance the rheological properties of water based fluids has been described. One approach to provide polyacrylamide based systems containing hydrophobic groups is described by Bock, et al., U.S. Pat. Nos. 4,520,182 and 4,528,358. Water soluble acrylamide copolymers containing a small amount of oil soluble or hydrophobic alkylacrylamide groups were found to impart efficient viscosification to aqueous fluids. Landoll, U.S. pat. No. 4,304,902, describes copolymers of ethylene oxide with long chain epoxides which also required relatively large polymer concentration (approximately 1%) for thickening water and required surfactants for solubility due to irregularities in the polymerization. In a related case, U.S. Pat. No. 4,428,277, modified nonionic cellulose ether polymers are described. Although these polymers show enhanced viscosification relative to polymers not containing hydrophobic groups, the viscosification efficiency was very low, requiring 2 to 3 weight percent polymer to provide an enhancement. The use of surfactants to enable solubility and, in turn, viscosification, by a water soluble polymer containing hydrophobic groups is described by Evani, U.S. Pat. No. 4,432,881. The hydrophobic groups claimed are attached to the polymer via an acrylate linkage which is known to have poor hydrolytic stability. In addition, the need for a surfactant to achieve solubility and thickening efficiency should make such a system very salt sensitive, as well as very sensitive to small changes in surfactant and polymer concentrations. Emmons, et al., U.S. Pat. No. 4,395,524, teaches acrylamide copolymers as thickeners for aqueous systems. While these polymers possess hydrophobic groups they are prepared using alcohol containing solvent which are known chain transfer agents. The resulting polymers have rather low molecular weights and, thus, relatively high polymer concentrations are required to achieve reasonable viscosification of water based fluids.

SUMMARY OF THE INVENTION

A process for producing a viscoelastic aqueous fluid utilizing a cationic polymerizable monomer which has been discovered to yield very efficient viscosifiers and rheological control additives for a variety of aqueous media. The process relies on the solubilization of specific cationic monomers containing relatively long alkyl functionality with specific anionically charged counterions. As a result, the hydrophobic monomer is completely capable of producing a clear, uniform, homogeneous solution even in the presence of other well-known water soluble acids, bases, salts and monomers. These solutions remains clear, uniform and homogeneous mixture with no phase separation. These cationic type monomers with the appropriate anionic counterion forms an unusual and unexpected morphology. These structures are rod-like micelles which are relatively large monomer aggregates consisting of many individual single monomer entities. Comparison of the rheological properties of these cationic monomer viscoelastic fluids with conventional hydrophobically associating polymers (previously described) confirms that the hydrodynamic size of the former structures are comparable to those of the latter polymers.

The viscoelastic fluids formed are very effective viscosifiers and rheological control additives having aggregation numbers, in the form of a rod, such that their intrinsic viscosities are greater than about 1 dl/g, but due to its unusual structure they are not at all susceptible to shear degradation as is observed in most high molecular weight polymers.

DETAILED DESCRIPTION OF THE INVENTION

The process of this invention overcomes the difficulties experienced in conventional polymeric viscosifiers and rheological control additives in aqueous media. In particular, it enables the efficient viscosification of aqueous fluids without the need for a moderate or high molecular weight water soluble polymer. The particular structures formed via monomers derived from the reaction of allyl halide with N,Ndimethylalkylamines are rod-like in nature and, as a result, aqueous solution containing these structures have properties comparable to relatively high molecular polymers. These structures form without he utilization of any other surfactant or rod-like polymers.

The process relies on the appropriate choice of an anionic counterion which is attracted to the cationic charge present on the cationic-hydrophobic monomer. The counterions are usually those that are not very soluble in water and surprisingly when attached to the cationic monomer spontaneously forms the rod-like structures resulting in viscoelastic monomer fluids. These fluids have solution properties comparable to excellent water soluble polymeric viscosifiers. It should be noted that dilute solutions of ionic and nonionic surfactants and detergents usually behave as Newtonian liquids, i.e. viscoelastic behavior is rare.

A criterion for the formation of these polymerizable cationic viscoelastic aqueous fluids can be approximated with the theoretical considerations of D. J. Mitchell and B. W. Ninham. J. Chem. Soc., Faraday Trans. 2,77, 601 (1981) and J. N. Israelachivili, D. J. Mitchell and B. W. Ninham, J. Chem. Soc., Faraday Trans. 2, 72, 1525 (1976). The first consequences of packing condition of these cationic monomers with the appropriate anionic counterion are applied under the assumptions of (1) constant volume v per monomer molecules and (2) constant headgroup area $a_o$ for a monomer molecule. In general, since the radius of the rod-like structure cannot exceed a certain critical length, $l_c$, roughly equal to but less than the fully extended length of the hydrocarbon, i.e. alkyl, group. It is shown by relatively simple packing considerations that rod-like structures (i.e. rod-like micelles) are able to form when the relationship $v/a_o l_c = \frac{1}{2}$, is approximately found.

It is known that viscoelastic surfactant fluids can be formed in aqueous media as described by H. Rehage and H. Hoffmann, Faraday Discuss. Chem. Soc. 76, 363 (1983).

The water soluble polymerizable monomers which produce these viscoelastic aqueous fluids of the instant invention are characterized by the formula:

wherein n is preferably 6 to 22 straight chained or branched chained alkyl or cycloalkyl group, more preferably 8 to 20 and most preferably 8 to 18. Typical, but not limiting examples of preferred alkyl groups are hexyl, octyl, decyl, dodecyl and steryl groups. Typical, but not limiting examples of preferred anionic counterion structures are salicylic acid and its metal neutralized salts, salicylates, methyl salicylic acid and its metal neutralized salts and methyl salicylates.

The solution of the instant invention comprises water or water having salt dissolved therein and about 0.1 to about 20.0 wt. % of the water soluble polymerizable monomer, more preferably 0.5 to about 10 wt. %, and most preferably 0.8 to 5.0 wt. %.

DESCRIPTION OF THE PREFERRED EMBODIMENT

The following examples explain the invention, which are by way of illustration, but not of limitation.

EXAMPLE 1

Cationic-Hydrophobic Monomer

Three representative examples for the synthesis of the following monomer structures to form these cationic viscoelastic monomer fluids is described below:

In these representative examples n=15 (11868-106A), n=13 (11868-106B) and n=17 (11868-106C).

Into a small round bottom flask add the following materials together and heat to 50° C. for four hours:

| | |
|---|---|
| 11868-106A | 14.2 g allyl bromine |
| | 31.6 g N,N-dimethyl dodecylamine |
| 11868-106B | 14.2 allyl bromide |
| | 28.3 g N,N-dimethyl tetradecylamine |
| 11868-106C | 14.2 g allyl bromide |
| | 34.9 g N,N-dimethyl octadecylamine |

The monomers are further purified through conventional analytical techniques. Elemental and NMR analysis confirms that the monomers are very pure (>99%) and has, in these specific examples, the following molecular structure:

EXAMPLE 2

Preparation of Cationic Polymerizable Viscoelastic Monomer Fluids

Representative examples for the preparation of cationic polymerizable viscoelastic monomer fluids containing the three above synthesized monomers are briefly described below.

Dissolve the monomer into water and subsequently dissolve a stoichometric amount of such compounds as salicylic acid-sodium salt or methyl salicylic acid, for example. It is noted that the requirement that a stoichometric amount of the latter compounds be used is not a necessary requirement. A relatively broad range of these materials can be used for effective utilization and preparation of these unique cationic monomer viscoelastic fluids. However, stoichometric amount of these compounds are used in the examples as a matter of convenience only. In any event, the viscosity of the fluid immediately increases to a value dependent upon the nature and concentration of the monomer and counterion.

EXAMPLE 3

Solution Behavior

Figure 1:
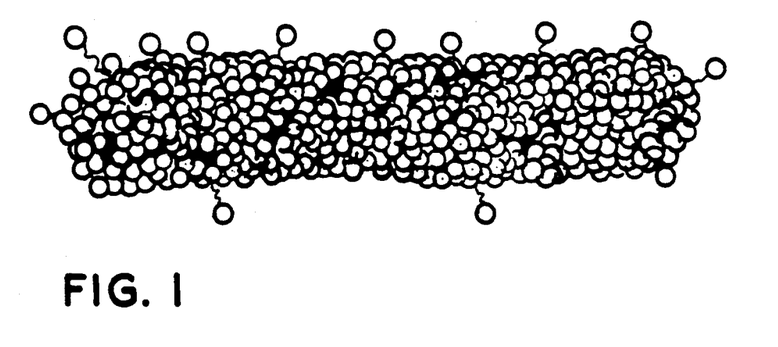
FIG. 1 illustrates a schematic drawing representing the external structure of an individual rod-like structure formed from the cationic monomers described within.
Figure 2:
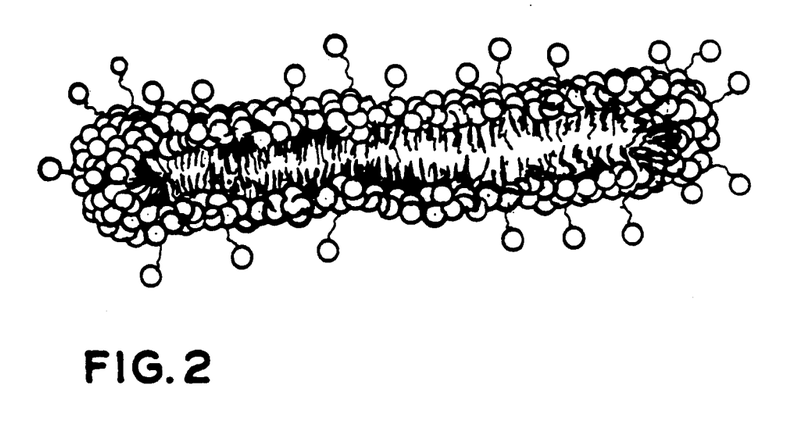
FIG. 2 illustrates a schematic drawing representing the internal structure of an individual rod-like structure formed from the cationic monomers described within.

It is anticipated that the morphology, i.e. structures, that these monomers can assume in solution is quite complex and undoubtedly, the dynamics of these structures can change rapidly with time, temperature, stress, strain rate, pressure, ionic strength and the like. However, our findings strongly indicate that the monomers form relatively large rod-like structures, as idealized in FIG. 1. In the figure, the spheres represent both the vinylic "head group" and the cationic region of the monomer. The alkyl "tails" are embedded in the rod interior due to well known hydrophobic interactions (i.e. charge-charge, purely geometrical-type rod overlappings and the like) that primarily contributes to the unusual rheology of these viscoelastic fluids. It should be noted, however, that the complete verification of the solution morphology does not in any way detract from the utilization of the novel properties of these viscoelastic fluids containing the above specific polymerizable cationic monomers.

Figure 3:
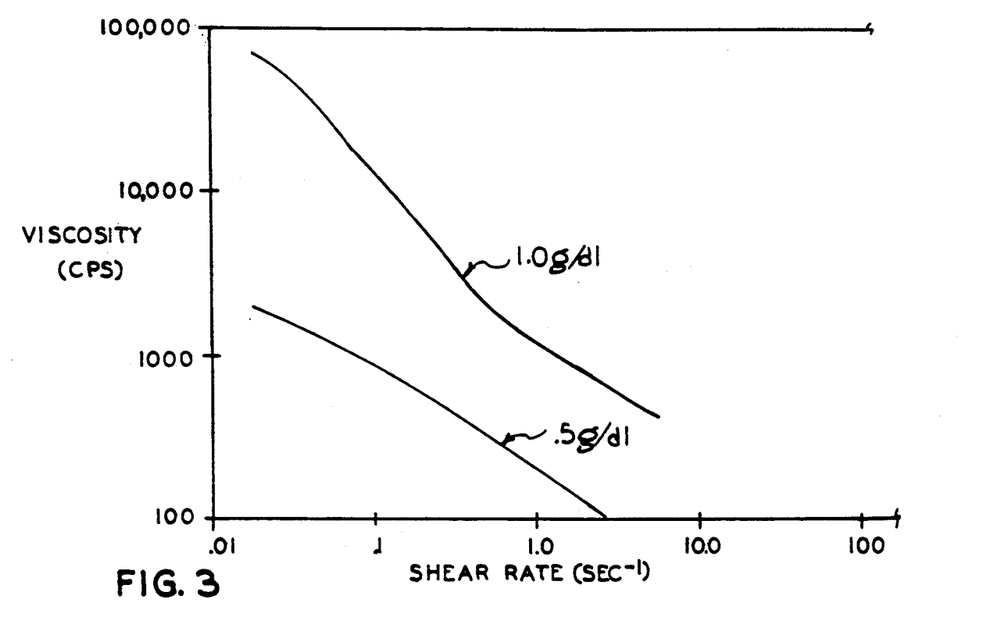
FIG. 3 illustrates a viscosity-shear rate profile of 11868-106A monomer solution with a molar ratio of methylsalicylic acid as a function of monomer concentration.

FIG. 3 shows some representative rheological properties of the above described cationic monomer viscoelastic fluids. An examination of this data clearly confirms:

1. At low monomer concentrations, very dramatic viscosity values are achievable.

2. At high shear rates, shear thinning characteristics are generally observed.

EXAMPLE 4

Figure 4:
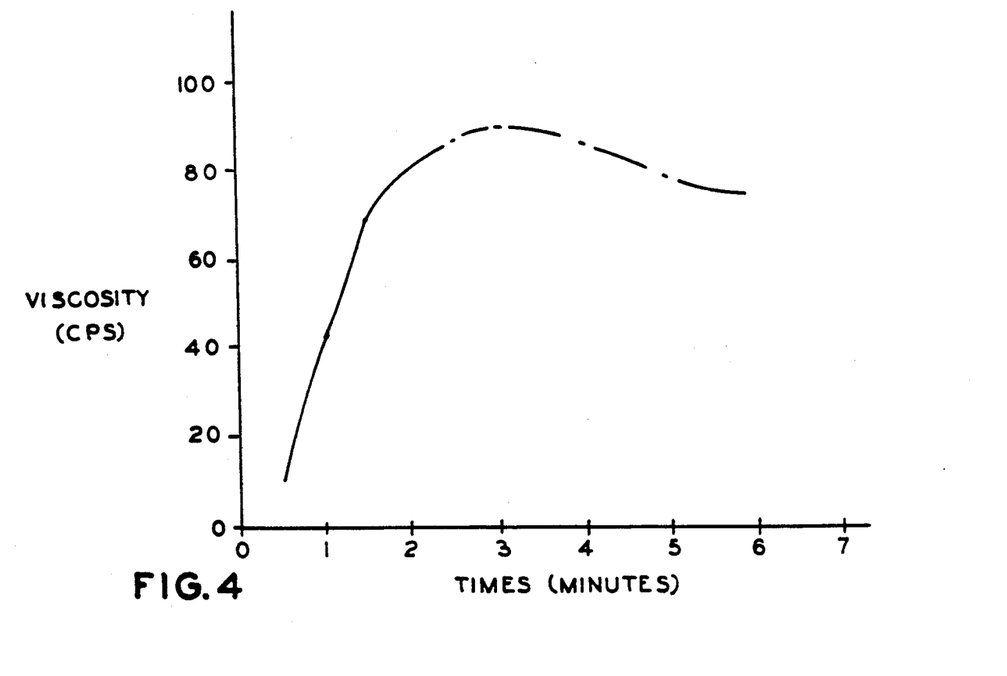
FIG. 4 illustrates a viscosity-shearing time of 1 g/dl 11868-106A monomer solution with a molar ratio of salicylic acid-solution salt. Shear rate is 0.017 sec$^{-1}$.

1. At low shear rates, marked time dependencies of the rheological properties are generally found. This is further shown in FIG. 4 in which the data of the 1g/dl fluid in FIG. 3 is expanded (i.e. low shear rate data).

2. Dilution causes a reduction in the magnitude of the rheological properties, in general.

EXAMPLE 5

Figure 5:
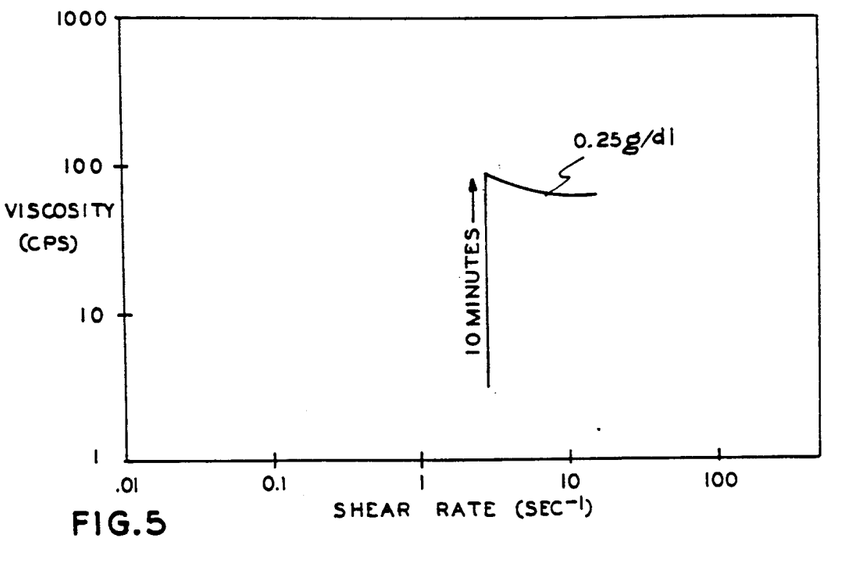
FIG. 5 illustrates a viscosity-shear rate profile of 11868-106A (0.25 g/dl) solution with a molar ratio of salicylic acid-sodium salt measurement temperature is 25° C.

1. The specific shear rate where the time dependency is found to occur is a strong function of the concentration (FIG. 5).

2. These viscoelastic cationic monomer fluids show dramatic shear thickening dependent upon concentration, molecular structure, counterion structure, temperature and the like.

3. Even though the molecular weight of the individual monomer units is quite low (<1000 g mole$^{-1}$, in general), the rheological properties of the fluid containing these monomers display high molecular weight polymeric properties.

EXAMPLE 6

1. All rheological, solubility etc. properties are a strong function of the alkyl length (n).

Figure 6:
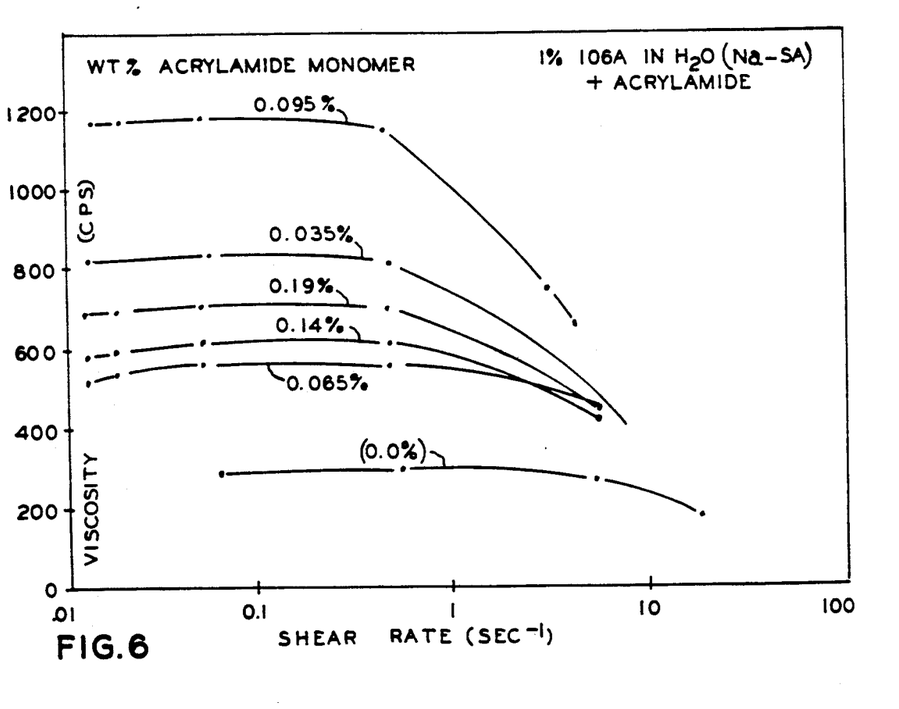
FIG. 6 illustrates a viscosity-shear rate profile of 1 g/dl solution of 11868-106A monomer with a molar ratio of sodium salt of salicyclic acid as a function of acrylamide monomer concentration.

2. Dissolution of nonionic polymerizable (and nonpolymerizable) moieties can, in specific instances, markedly enhance the rheological properties of the aqueous cationic monomer viscoelastic fluids (FIG. 6).

EXAMPLE 7

Figure 7:
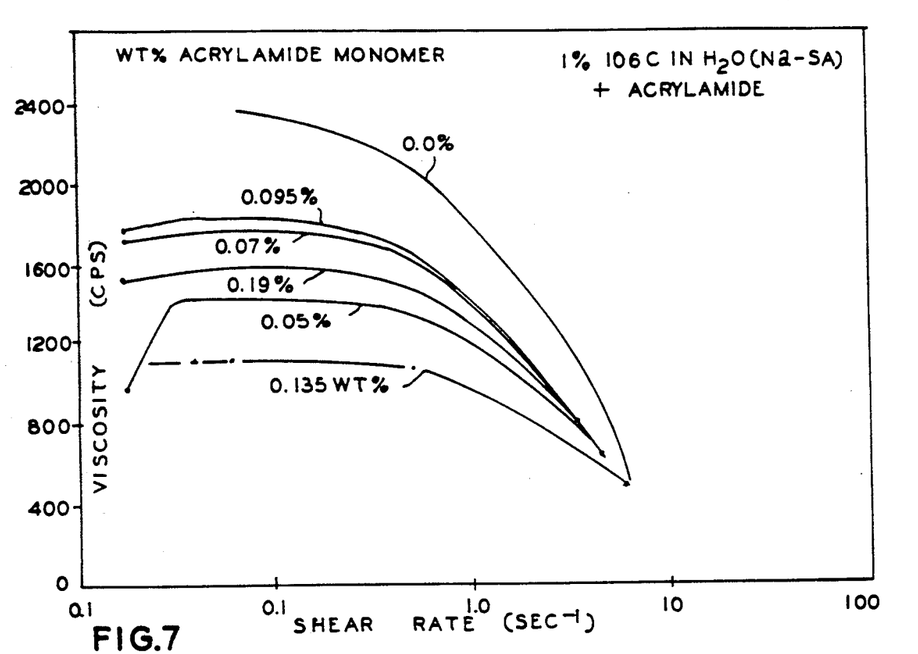
FIG. 7 illustrates a viscosity-shear rate profile of 1 g/dl solution of 11868-106C monomer with a molar ratio of sodium salt of salicylic acid as a function of acrylamide monomer concentration.
Figure 8:
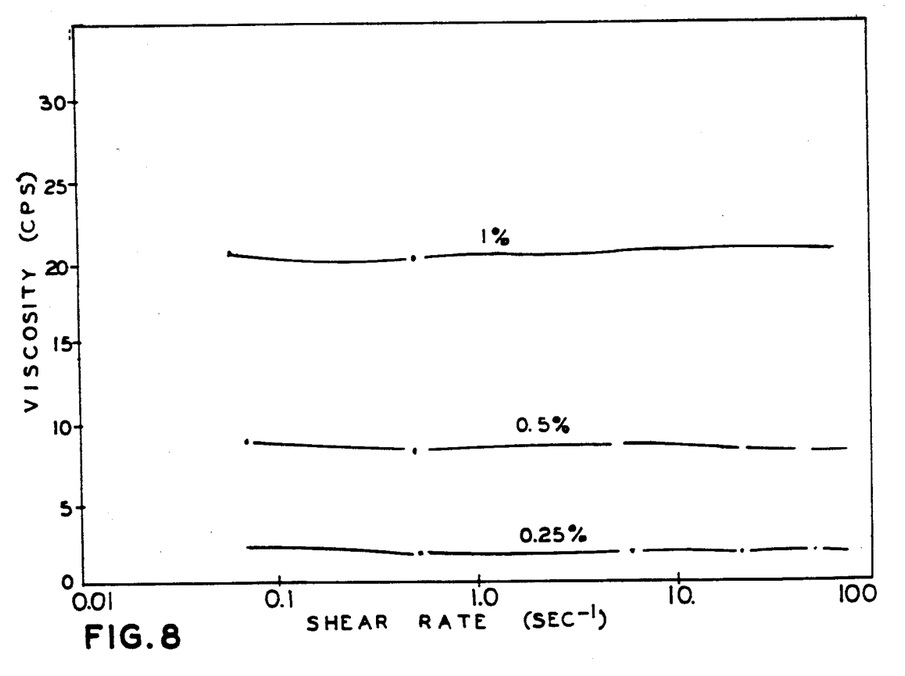
FIG. 8 illustrates a viscosity-shear rate profile of 11868-106B (1:1 molar ratio of salicylic acid-sodium salt) as a function of concentration (g/dl).
Figure 9:
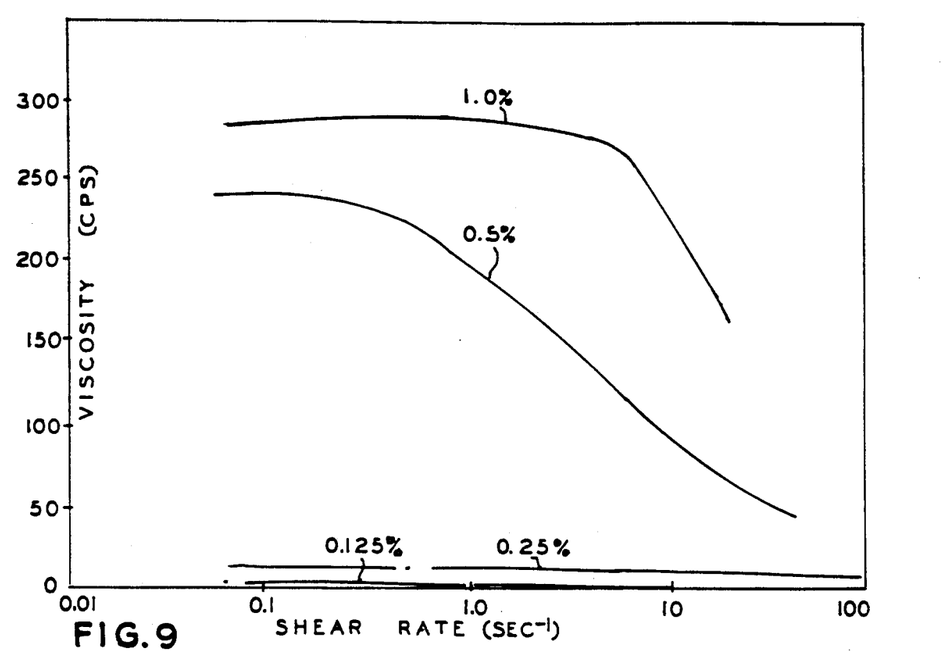
FIG. 9 illustrates a viscosity-shear rate profile of 11868-106A monomer (1:1 molar ratio of salicylic acid-sodium salt) as a function of monomer concentration (g/dl).
Figure 10:
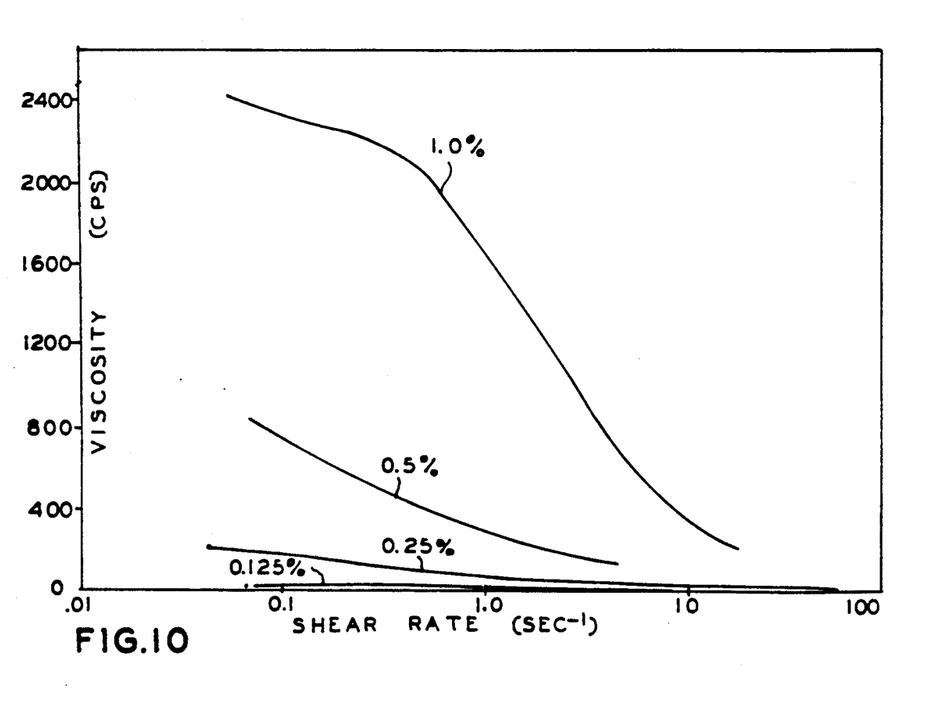
FIG. 10 illustrates a viscosity-shear rate profile of 11868-106C monomer (1:1 molar ratio of salicylic acid-sodium salt) as a function of monomer concentration (g/dl).
Figure 11:
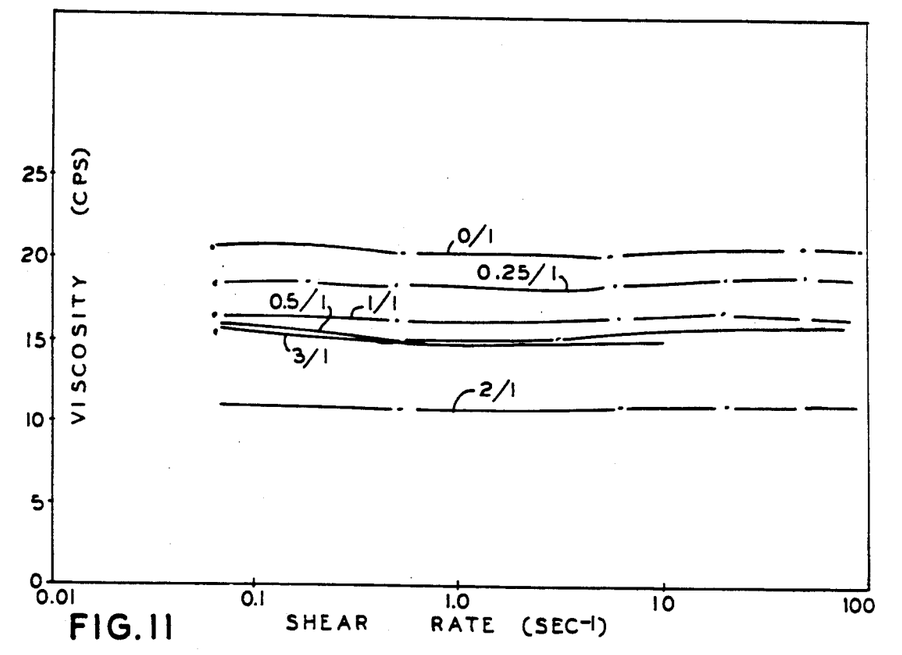
FIG. 11 illustrates a viscosity-shear rate dependence of a 1.0 g/dl 11868-106B monomer solution as function of various ratios of sodium chloride to monomer, i.e. [NaCl]/[monomer].
Figure 12:
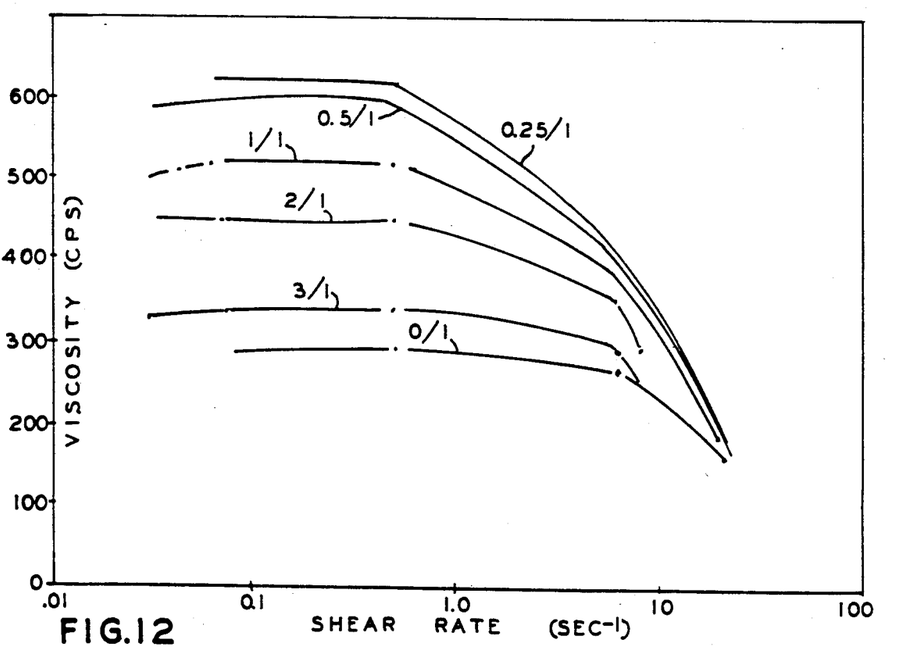
FIG. 12 illustrates a viscosity-shear rate profile of a 1.0 g/dl 11868-106A monomer solution as a function of various ratios of sodium chloride to monomer [NaCl]/[monomer].
Figure 13:
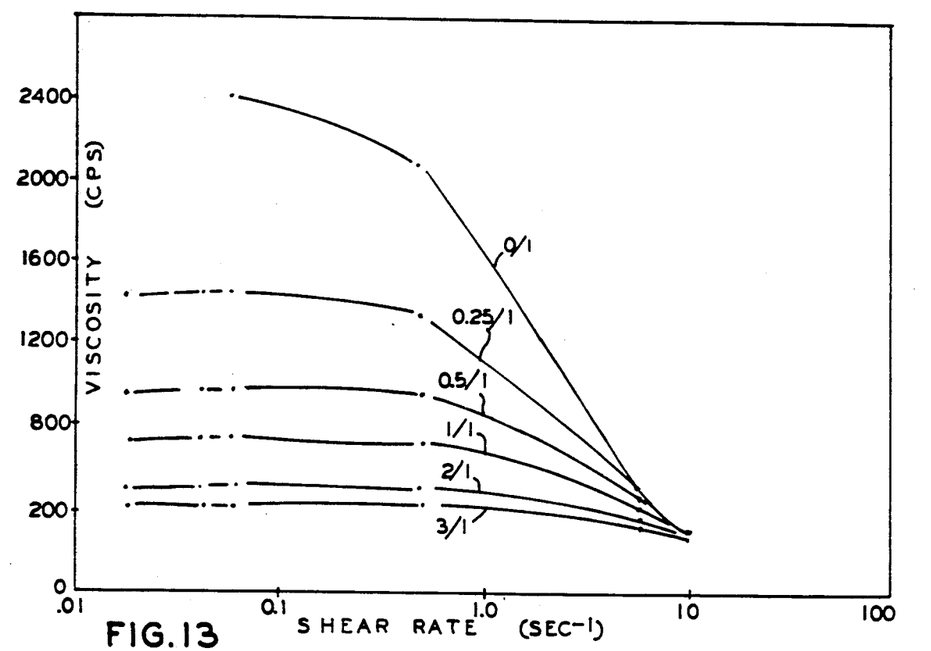
FIG. 13 illustrates a viscosity-shear rate dependence of 11868-106C monomer solution (1g/dl) as a function of various ratios of sodium chloride to monomer.
Figure 14:
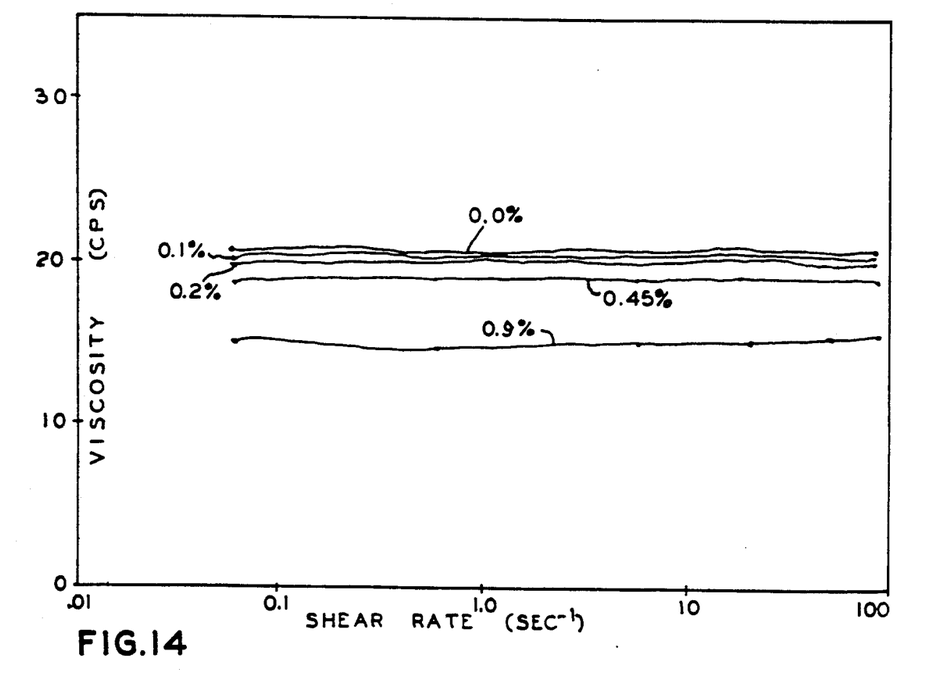
FIG. 14 illustrates a viscosity-shear rate profile of a 11868-106B monomer solution (1 g/dl) as a function of various concentrations of calcium chloride.

1. Dissolution of nonionic polymerizable (and nonpolymerizable) moieties can, in specific instances, markedly reduce the rheological properties of the aqueous cationic viscoelastic fluids (FIG. 7). It should be noted, however, that the rheological properties of the fluids are still both scientifically interesting and technologically useful. Apparently, the principal reason for the reduction in the solution properties is due to the reduction in the solubility of either the individual monomer entities and/or the rod-like structures themselves.

We note at this point that the synthesis, preparation and utilization of cationic polymerizable viscoelastic monomers and fluid compositions is useful to impart improved and useful rheological properties to aqueous fluids. The specific properties can be varied over a very broad range due to the ability to readily modify or change a number of compositional variables in the monomer and/or counterion structure.

These types of monomer containing aqueous viscoelastic fluids are useful as rheological control additives in a variety of drilling operations. Included in this category are a variety of well control and workover fluids, fracturing fluids, brine viscosifiers, gelation agents, foaming additives, completion fluids, enhanced oil recovery, drag reduction agents and the like.

EXAMPLE 8

Solution Behavior In High Ionic Strength Solutions

It is anticipated that the morphology, i.e. structures, that these monomers can assume in solution is quite complex and undoubtedly, the dynamics of these structures can change rapidly with time, temperature, stress, strain rate, pressure, ionic strength and the like. However, our findings strongly indicate that the monomers form relatively large rod-like structures. It is the large dimensions of the individual rods and their interactions (i.e. charge-charge, purely geometrical-type rod overlappings and the like) that primarily contributes to the unusual rheology of the viscoelastic fluids. It should be noted, however, that the complete verification of the solution morphology does not in any way detract from the utilization of the unique properties of these viscoelastic fluids containing the above specified polymerizable cationic monomers.

FIGS. 8-16 show some representative rheological properties of the above described cationic monomer viscoelastic fluids. The solutions in these specific examples are either fresh or brine (sodium chloride and calcium chloride) solutions. An examination of the data clearly confirms the following conclusions:

1. The rheological properties in fresh water of these cationic monomers with salicylic acid-sodium salt as the counterion are a strong function of the alkyl length, n ($C_{13} < < C_{16} < < C_{18}$).

2. At relatively low monomer concentrations, very dramatic viscosity is observed. These values are a strong function of the alkyl length (FIGS. 8-11).

3. Dissolution of acid, base and salt, can in specific instances, markedly enhance the rheological properties of the aqueous cationic viscoelastic fluid (FIGS. 12-16). The specific viscosity value change is a strong function of the alkyl length, n, in these cationic monomers, i.e. $C_{18} < < C_{14} < < C_{16}$. In fact, 106A displays a dramatic rise in viscosity with salt (NaCl) concentration. 106B and 106C shows a reduction in viscosity in the same salt concentration range.

Figure 15:
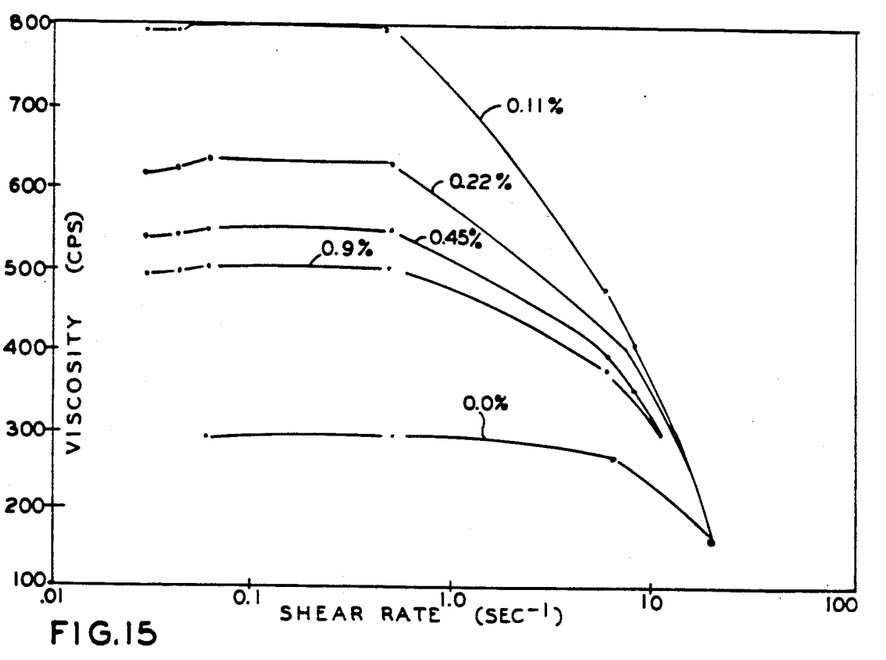
FIG. 15 illustrates a viscosity-shear rate profile of a 1.0 g/dl 11868-106A monomer solution as a function of calcium chloride concentration (wt. %).
Figure 16:
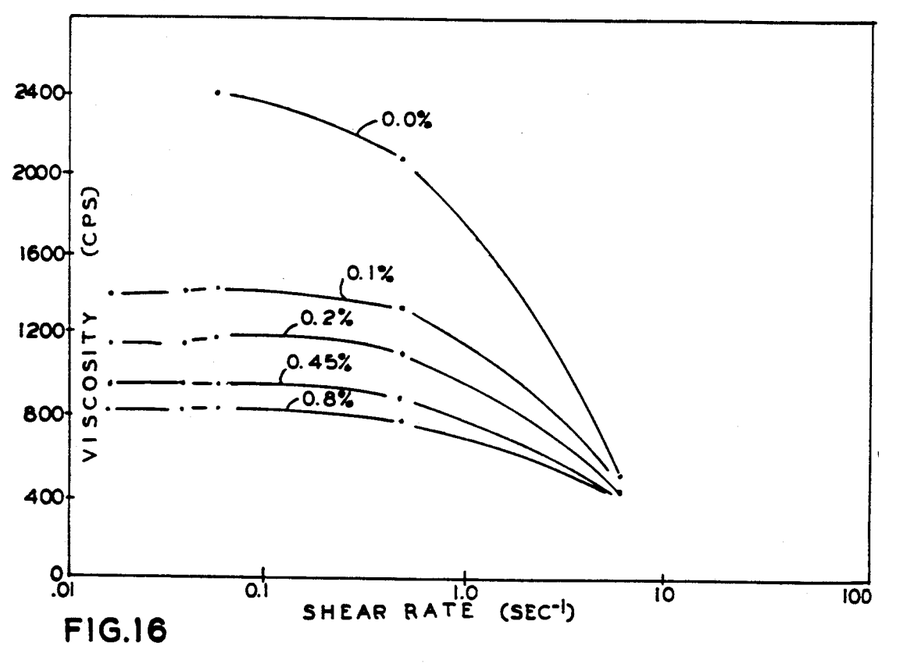
FIG. 16 illustrates a viscosity-shear rate profile of 1.0 g/dl 11868-106C monomer solution as a function of calcium chloride concentration (wt. %).

4. Similar observations as in 3 are noted in solutions containing high levels of calcium chloride (FIGS. 15-16).

5. From the results it is clearly found that ion-exchange is not a dominant factor, in these specific monomer solutions, in determining structural stability until very high levels of salt are reached.

Again in summary, the utilization of cationic polymerizable, viscoelastic monomers and fluid compositions is noted to impart improved and useful rheological properties to fresh and high brine solutions. The specific properties, as notes within, can be varied over a broad range due to the ability to modify a number of compositional and structural variables in the monomer and/or counterion structure.

These types of monomers containing high brine viscoelastic fluids are useful as rheological control agents in a variety of drilling and completion fluids, especially where high brine solutions are used or found.

What is claimed is:
1. A solution comprising:
  (a) water; and
  (b) about 0.1 to about 20.0 wt. % of a water soluble polymerizable monomer characterized by the formula:

wherein n is 6 to 22.
2. A solution according to claim 1, wherein n is 13.
3. A solution according to claim 1, wherein n is 15.
4. A solution according to claim 1, wherein n is 17.

* * * * *